United States Patent [19]

Van der Merwe et al.

[11] Patent Number: 4,478,946
[45] Date of Patent: Oct. 23, 1984

[54] CARRIER BOUND IMMUNOSORBENT

[75] Inventors: Kirsten J. Van der Merwe, Stellenbosch; Alfred Polson, Camps Bay, both of South Africa

[73] Assignee: South African Inventions Development Corporation, Pretoria, South Africa

[21] Appl. No.: 392,111

[22] Filed: Jun. 25, 1982

[30] Foreign Application Priority Data

Jul. 2, 1981 [ZA] South Africa .................. 81/4481

[51] Int. Cl.³ .................. G01N 33/54; G01N 33/56
[52] U.S. Cl. .................. 436/518; 436/524; 436/527; 436/532; 435/7
[58] Field of Search .................. 436/518, 523–535, 436/823

[56] References Cited

U.S. PATENT DOCUMENTS

| | | | |
|---|---|---|---|
| 3,646,346 | 2/1972 | Catt | 250/83 |
| 3,790,663 | 2/1974 | Garrison | 424/12 |
| 3,985,617 | 10/1976 | Yugari et al. | 435/176 |
| 4,043,869 | 8/1977 | Barker et al. | 260/112 R |
| 4,123,396 | 10/1978 | Rembaum et al. | 427/222 |
| 4,170,685 | 10/1979 | Rembaum et al. | 204/159.15 |
| 4,197,220 | 4/1980 | Rembaum | 436/56 |
| 4,267,234 | 5/1981 | Rembaum | 256/62.54 |
| 4,280,816 | 7/1981 | Elahi | 23/915 |
| 4,338,094 | 7/1982 | Elahi | 23/915 |
| 4,369,226 | 1/1983 | Rembaum | 424/32 |

FOREIGN PATENT DOCUMENTS 2951412 7/1981 Fed. Rep. of Germany .

OTHER PUBLICATIONS

Hodes, M. E. et al., J. Chromatography, vol. 104, pp. 379–387, (1975).
Rembaum, A., Pure and Applied Chemistry, vol. 52, pp. 1275–1278, (1980).

Primary Examiner—Benjamin R. Padgett
Assistant Examiner—M. Moskowitz
Attorney, Agent, or Firm—Millen & White

[57] ABSTRACT

The invention provides an immuno-reactant, being either an antigen or an antibody covalently bonded to a cross-linked film, more particularly composed of cross-linked protein or peptides, enveloping a carrier body, e.g. a solid, non-porous glass bead of 6 mm diameter. The immuno-logically active parts of the immuno-reactant are present on the surface in a form in which they are available for immunosorption. If the immuno-reactant is a protein, e.g. an antibody, it can provide all or part of the film-forming material. In a particular embodiment the film carries antibodies against a second type of antibody which is captured immunosorptively to form a "double layer" carrier-bound immunosorbent, the antigen capturing sites of the second type of antibody providing the immunosorption sites of the product. The immunosorbents are used, for example, for RIA or ELISA assays.

50 Claims, 7 Drawing Figures

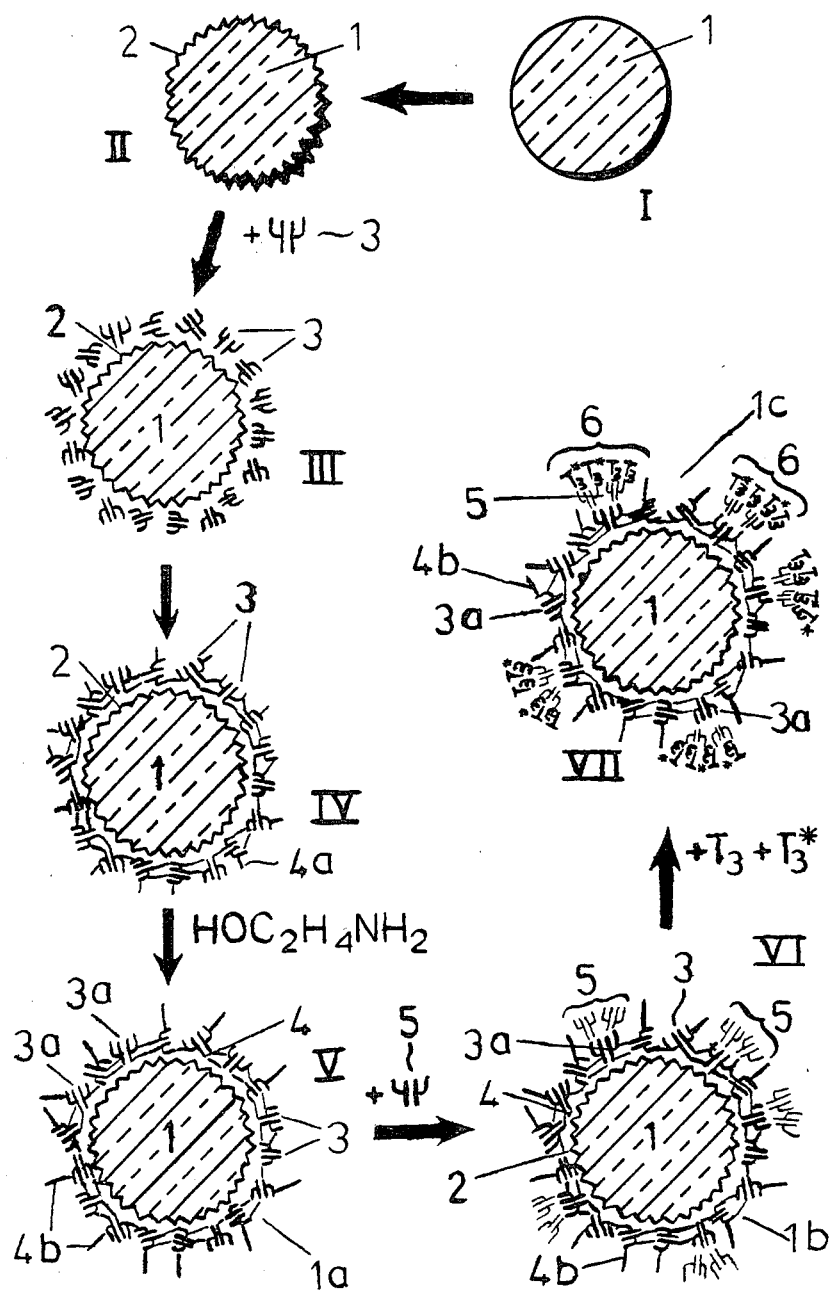

CARRIER BOUND IMMUNOSORBENT

BACKGROUND OF THE INVENTION

The present invention relates to a carrier-bound immunosorbent comprising a carrier body carrying an immobilised immuno reactant.

Immobilised antibodies cross-linked by covalent bonding, e.g. with a cross-linking agent such as glutaraldehyde, to a carbohydrate type of carrier, e.g. cellulose or agarose are known (R. Kowal et alia, anal. Biochem. 102, 72-76 (1980)). The carrying capacity of these carbohydrates is comparatively low and the products are not very stable.

T. T. Ngo (Int. J. Biochem Vol. 11, pages 459-465) describes a variety of immobilised enzyme systems—but not in the context of immuno reagents—in which the enzymes are immobilised (a) by adsorption (such enzymes becoming easily desorbed);
(b) by covalent attachment of their non-essential amino acid residues to "chemically activated supports" such as cellulose, glass or synthetic polymers via azide, isocyanate, carbodiimide and other derivatives of the supports,
(c) polycondensation by cross-linking of the enzymes themselves, using bifunctional cross-linking agents such as diisothyocyanate, bisimidates, alkylating agents and dialdehydes to form aggregates in which, however, a major part of the desired characteristics of the enzymes is lost.

Enzyme-linked immunosorbents for use in assays (Elisa) for specific antibodies are known (A Voller et alia, proc. soc. exp. biol. med. 163, 402-5 (1980)). Immunoreactants bonded to a substrate by adsorption or ion exchange had been known, but the bond is weak.

Sportsman and Wilson (Anal. Chem. (1980), 52, 2013-2018) describe antibodies covalently bonded via their protein amine groups (by Schiff reaction followed by reduction with sodium borohydride) to aldehyde groups formed by periodate oxidation of glycidoxypropylsilane groups chemically linked to the silica atoms of silanised porous glass micro beads serving as carrier bodies. The porous glass beads having a diameter of 10 micron are silanised by immersion in a solution of glycidoxypropyltrimethoxysilane (GOPS). This results in the individual silane molecules attaching themselves chemically to individual silicon atoms of the silica of the glass. The organic glycidoxypropyl groups are converted by oxydation into aldehyde groups which in turn are reacted with the antibodies which are thereby immobilised. Immunosorbtive characteristics of the resulting carrier-bound immunosorbents are studied by observing the performance of chromatographic columns packed with the micro beads. For that purpose two antigens (human IgG and beef insulin) are first immunosorbed and then released by lowering the pH and with acetonitrile respectively. The immunosorbent is prepared specially using a different antibody for each antigen. Neither anti-insulin nor anti-human IgG antibodies are suitable for manufactured immunosorbents having a wide spectrum of uses. The method is of limited scope as regards chemical groups (amino) of an immunoreactant which can be used for the immobilising reaction as well as the geometry of the linkage and in particular the chemical and physical nature of the carrier body and its surface. It is not always desirable that the carrier body should have a silicious surface or have the physical properties of silica or glass (e.g. if metallic or magnetic properties would be useful). Also it is not always desired that the immobilised member of an antibody/hapten (antigen) pair in an immunosorption reaction should necessarily be the antibody.

The prior art silanisation of the glass particles will result in a "covering" of the glass surfaces which will normally be no more than monomolecular but may be even less. Such a "covering" will not as a rule avoid non-specific and easily reversible absorption of test substances, and this will interfere with desired forms of specific and strong immunosorption. Exposed siliceous adsorption sites and polar groups on glass surfaces tend to denature sensitive proteinaceous compounds. The porosity of the prior art microbeads, whilst desirable for some purposes, is a distinct disadvantage in the preferred field of application of the present invention. It influences the surface area unpredictably and in a manner which may vary from one bead to another. Such porosity has a molecular sieve effect whereby exclusion and molecular size-dependent retention effects are superimposed on and interfere with the desired selective and pure immunosorbtive effects. The smallness of the prior art beads makes them unsuitable for specific uses which the present invention contemplates.

The prior art carrier-bound immunosorbents each lack one or more of the following desirable qualities to a greater or lesser degree: stability, universal applicability, high capacity, ease of standardisation.

SUMMARY OF THE INVENTION

It is an object of the invention to overcome or mitigate the aforesaid drawbacks or limitations of the prior art and to provide novel carrier-bound (immobilised) immunosorbents of great adaptability to a highly variable range of uses, which have a desired degree of stability, the capacity of which can be tailormade to a desired level, which can be readily standardised. More particularly, it is an object to provide a new type of carrier-bound immunosorbents which can be easily adapted and applied to a wide variety of immunosorbtive assays, e.g. for diagnostic, micro analytical, forensic and pharmacokinetic work.

The present invention may be considered from a plurality of aspects, all of which may apply in combination to certain preferred embodiments.

According to a first aspects of the invention, a carrier bound immunosorbent as set out in the opening paragraph is provided, wherein the immuno reactant, being either an antigen or an antibody, is covalently bonded to a cross-linked film enveloping the carrier body in such a manner that immunologically active parts of the immuno reactant are present on the surface in a form in which they are available for immunosorption. Preferably they are exposed and project from the film.

Immunogen and antigen are used substantially synonymously in the present context.

The following definitions apply in the context of the present specification.

Immunogen: An immunogen is a foreign substance e.g. protein or particle, e.g. virus or bacterium, which can by itself induce an immune response which usually results in the appearance of antibodies (Ab) e.g. in the circulation of an animal the immuno system of which is exposed to the immunoger, e.g. by injection.

Antigen: An antigen (Ag) is a substance or particle which can bind to its specific antibody to form an Ab-Ag complex, called an immune complex, but which will not necessarily induce an immune response by itself.

Hapten: A hapten is a substance, generally of low molecular weight, incapable of eliciting antibody formation by itself, but able to react with an antibody and to become immunogenic when coupled to a carrier.

Immuno-reactant: a substance capable of being one of the reaction partners in an antibody/antigen (or hapten) complex formation.

Preferably the film comprises cross-linked protein molecules or their peptide portions. Preferably the immuno reactant itself provides the protein molecules or peptide portions or at least a substantial part thereof. In this context it is pointed out that all antibodies and a high proportion of important antigens are proteins.

As regards the cross-linking agents which may be used for cross-linking the film constituents, reference is made to the description of the process in accordance with the invention which follows further below.

The film may include a cross-linked additional film-forming substance, preferably a protein or peptide, other than the immuno reactant. This applies particularly in two situations:

(a) if the immuno reactant is not available in sufficiently large quantities to provide all the film-forming material needed; and (b) if the immuno reactant itself taken alone does not form a satisfactory film. In that case the immuno reactant may be attached covalently onto a film-forming material, e.g. with one or more bifunctional reagents having at least one functional group reactive to the additional film-forming substance and at least one functional group reactive to bond to a reactive site of the immuno reactant, preferably a site, the loss of which has no or as little as possible effect on the desired immunological properties of the immuno reactant. Once again, as regards a fuller description of the bifunctional reagents, reference is made to the description of the process further below.

A preferred film-forming substance is gelatine, gelatine derived from bones being particularly preferred. However, gelatine derived from hides, e.g. pigskins, or from collagen may be used as well. If desired or required, the gel strength of the gelatine may be increased, e.g. as described in U.S. Pat. No. 3,640,809. Alternative additional film-forming substances are albumins, e.g. ovalbumin, serum albumin (not preferred) and generally basic proteins.

The immuno reactant may be present in the film in random mixture with the additional film-forming substance. Alternatively, the additional film-forming substance may envelop the carrier body alone and has bonded to its exposed surface(s) the immuno reactant, e.g. bonded thereto with the aid of a cross-linking or bifunctional reagent as aforesaid.

The term "film" in the context of the present specification does not necessarily imply an impervious or dense layer, since the main criterion is the cohesiveness of the film for adequately strong enveloping of the carrier body. However, as a rule it is preferred that the film should cover the surface of the carrier body substantially completely.

In this respect the present aspect of the invention differs from the disclosure by Sportsman and Wilson in that it relies on the mechanical envelopment of the carrier body by the film rather than one chemical bonding to the surface of the carrier body itself. Moreover, if in accordance with the preferred embodiments the carrier body is covered completely by a proteinaceous film the risks of non-specific adsorption and of damage to sensitive substances to be immunosorbed is minimized.

The amount of immuno reactant bonded onto the carrier body per unit of surface area of the carrier body will obviously depend to some extent on the molecular weight of the immuno reactant. In the case of a typical proteinaceous immuno reactant in a molecular or particle mass range of from 300 through $8 \times 10^6$ and higher (bacteria for example) as single particle or molecular layers the amount will be usually within the range of 30 mg per m$^2$ (e.g. for polio virus which has a particle diameter of $30 \times 10^{-7}$ cm (30 nm) and influenza virus 120 mg/m$^2$ which has a diameter of $120 \times 10^{-7}$ cm (120 nm)) to 1 mg/m$^2$ for substances such as insulin which have particle diameters of the order of $1 \times 10^{-7}$ cm (1 nm).

Some haptens which may serve as immuno reactants are even smaller. However, usually the amount would be greater because in preferred embodiments multiple layers of the antigens are cross-linked on the surfaces of the bodies because of the pitted surfaces of the bodies. Of these amounts, e.g. if insufficient immuno reactant is available or if the immuno reactant itself is unsuitable for film formation, between 30% and 1000%, preferably not more than 300% by weight may be replaced or supplemented by a different protein or peptide extender.

This means that the amount of antigen substance forming the whole of or a part of the film will generally be in the range of about 0.6 to 500 mg/m$^2$, depending on the antigen or antibody size and on whether or not an additional film-forming substance (extender) is used.

The carrier body preferably has a configuration suitable for being enveloped in such a manner that the film does not come off easily. The carrier body may take the form of a rod, e.g. a glass rod which can be dipped into a fluid on which an assay is to be conducted. More preferred are solid bodies or particles of a defined fully immersable shape, preferably solid beads of roundish, more particularly spheroidal or better still spherical configuration, e.g. glass beads or magnetically attractable beads, e.g. of stainless steel. Such beads should preferably have a density higher than 1, so that they will readily sink in an aqueous liquid. In contrast to the aforesaid teachings of Sportsman et al the beads of the preferred embodiments of the invention are solid, non-porous and have diameters several orders of magnitude larger, According to a particular embodiment protein A or concanavillin A is covalently bonded to the film and in its turn carries selectively captured antibody molecules, held by the tail ends of the molecules. Protein A and concanavillen A both have the property that they can capture and strongly hold a large number of antibodies in a manner very similar to immunosorptive mechanisms. The antibodies so captured will then in turn provide outwardly facing immunosorption sites for antigens to such antibodies.

According to a second aspect of the present invention, there is provided a carrier-bound immunosorbent as set out in the opening paragraph, comprising the feature that the surface of the carrier body or a film coated thereon carries covalently bonded thereto a first immuno reactant being one member of an immunogen-/antibody pair and the first immuno reactant holding by immunogen/antibody interaction the second member of the pair, this second member projecting from the surface with a region thereof which itself in turn has a desired immuno reactivity for entering into an immunosorbent reaction with a third immuno reagent.

There is thus present a kind of "double layer" of immuno reactant, the first layer being usually bonded to the solid substrate in random orientation, but still including an adequate amount of immuno reactant so orientated as to be capable of capturing and holding an adequate amount of immuno reactant forming the second layer. The molecules of this immuno reactant of the second layer have one distinct portion capable of being immunosorbed by the immuno-reactive counterparts of the first layer and another portion capable of in turn immunosorbing whatever immuno reactant the product according to the invention is intended to be an immunosorbent for. This second portion will invariably be so orientated as to project in an outward direction away from the substrate, i.e. away from the "first layer". The specific binding sites of the second layer will be exposed and free to react with their antigens. The "second layer" may in turn be fixed in place by covalent bonding by means of a suitable linking reagent as referred to above, although this is not preferred.

Preferably a product as described in connection with the first aspect of the invention may serve as an intermediate for making the product according to the second aspect of the invention. Moreover, the various essential and/or preferred features of products according to the first aspect of the invention are preferably incorporated in the products according to the second aspect of the invention.

The scope of the invention extends to the process and product of converting that intermediate by exposing it to an aqueous solution or suspension of the immunoreactant which is to serve as the "second layer", thereby to "capture" immunosorbtively the "second layer". This process can be carried out under standardised conditions so that the "second layer" may have a standardised amount of desired immuno-reactive sites. This is achieved by applying a known amount of "second layer" immunoreactant which is sufficient to only partially saturate the available sites provided by the "first layer".

The process described in the preceding paragraph may also be considered an embodiment of a method of using an immunosorbent according to the invention which comprises bringing such immunosorbent which carries exposed on its surface an immobilised immunoreactant specific to immunogenic determinants present on a first substance of a mixture and not on other substance(s) of the mixture, into intimate contact with the mixture, thereby selectively immunosorbing the first substance and removing the immunosorbent from contact with the mixture.

In accordance with a preferred embodiment, the aforesaid intermediate (which represents a useful commercial product as such) comprises as the first-layer immuno-reactant antibodies against a particular immunogenic molecular region which in its turn can be readily incorporated (as the matching counterpart for being captured by the "first layer") in the molecules (usually forming one end of a macromolecule) of a wide variety of immuno reactants desired to form the "second layer", e.g. a wide variety of highly specific antibodies for various immuno assays. In practice this may mean for example that the first layer is formed from antibodies raised specifically against antibodies in general obtained from a specific animal, e.g. mammalic serum IgG (rabbit, or sheep or horse or any other suitable animal) raised against IgY recovered from the yolk of fowl eggs and serving as the antigen; or mammalic serum IgG of one mammal raised against a different mammal. Such a "first layer" will then have no specifically except that of capturing all antibodies derived from the specific species of animal (and in the specific example of antibodies against IgY will selectively capture any specific antibodies as long as they have been obtained from the yolk of fowl eggs).

This "intermediate" is a valuable commercial product per se, namely where it is intended that the end user itself should select and apply the immuno reactant (e.g. a monospecific antibody, e.g. mono-specific IgY) to complete the "double layer" required for a specific test. Such monospecific antibodies may be made available commercially for the purpose or may be prepared by the end user in accordance with instructions given by the manufacturer. Since a specific "first layer" antibody will bind any "second layer" antibody of the correct origin (i.e. raised or elicited in an animal against which the "first layer" antibody is specific; or so raised or elicited and subsequently reproduced by tissue culture, e.g. monoclonal tissue culture) it will be understood that glass beads or the like covered with one particular type of "first layer" antibodies can be used in many different assays (e.g. different ELISA or RIA's), determined solely by the choice of antibodies for the "second layer".

For the raising of special and highly specific antibodies, in particular for the "second layer" the person skilled in the art has available numerous known techniques, including what is disclosed in U.S. patent application Ser. No. 020,786, UK patent application No. 79 307 64, Japanese patent application No. 54-73150 and West German Offlenlegungsschrift No. 2951412. As part of the present disclosure, particularly in the present context, reference is also made to the teachings of South African patent application No. 81/4898 and to patent applications filed or to be filed in USA, UK, Federal Republic of Germany, Japan and South Africa claiming a priority based thereon.

If further purification to increase the specificity is desired or required, this is achieved by known techniques or by using an immunosorbent according to the present invention as a separating medium in an immunosorbtive separation; or by fractional precipitation in a selected pH range, e.g. with a polyalkyleneglycol, e.g. polyethylene glycol. This latter procedure is based on the not previously known inventive concept that antibodies against immunogens of different molecular weights have different isoelectric pH valves. They accordingly have minimum solubilities at different pH values.

Inter alia, usable for the aforesaid purpose the present invention provides (as an embodiment of the method of use set out above) an immunosorbtive separating process which comprises bringing an immunosorbent according to the invention as set out in the aforegoing, carrying an immobilised immuno-reactant specific to immunogenic determinants present on a first substance of a mixture and not on other substance(s) of the mixture into intimate contact with the mixture, thereby selectively immunosorbing the first substance, removing the immuno-sorbent from contact with the mixture and desorbing the first substance to release it from the immunosorbent in purified form. Suitable desorbent conditions for this purpose are known per se. A weak acid, e.g. propionic acid is a suitable desorbent, e.g. at pH 3-4, say 3.5 for releasing some immunosorbed substances. Other examples are acetonitrile or glycine-HCl buffer (pH 2.6-2.9).

From the aforegoing emerges as a third aspect of the present invention a carrier bound immunosorbent as broadly set out in the opening paragraph, comprising on a solid substrate a first layer including covalently bonded and cross-linked antibodies of a first species of animal raised against antibodies of a second species of animal and a second layer immunosorbed on the first layer of specific antibodies elicited against a specific antigen in the second species of animal. For certain purposes, e.g. where the binding or other properties of IgY are particularly superior (higher stability, higher avidity, better availability, freedom from proteolytic enzymes). The second species is preferably a bird, e.g. a fowl species, more particularly a domestic chicken, and more particularly the antibodies elicited in the bird are recovered from the egg yolk of an egg or eggs of such bird.

As regards the production of IgY from the yolks of domestic fowls, reference is made to the disclosures contained in U.S. patent application Ser. No. 020,786, UK patent application No. 79 307 64, Japanese patent application No. 54-73150 and West German patent application No. P 29 51 412, which by reference thereto are to be considered as part of the present disclosure.

Also in accordance with the invention, there is provided a method of using the preparation in accordance with the invention which comprises intimately contacting immobilised immunosorbent in accordance with the invention, having exposed on its surface a standard amount of a first immuno-reactant specific to a complementary second immuno-reactant of an antigen/antibody pair to a solution of the second immuno-reactant and determining the amount of the second immuno-reagent in the solution which becomes attached to the immunosorbent.

According to one modification (particularly suitable for the determination of comparatively large antigens) the immunosorbent loaded with immuno reactant captured from the sample is immersed in a solution of a labelled immuno reagent complementary to the captured immuno reactant. The dissolved immuno reagent may be labelled with an enzyme capable of producing a measurable colour reaction with its substrate or may be labelled with a radioactive isotope. (The substrate is a substance, the decomposition or alteration of which is catalytically accelerated by the particular enzyme). The amount of labelled substance may be determined directly on the glass beads or by subtraction in the residual reagent solution.

Alternatively (e.g. where it is desired to determine the concentration of comparatively small antigens) the antigen sample solution may be mixed with a known volume of a standard solution containing the same immuno reactant in a labelled form and the mixture is contacted with the immunosorbent according to the invention, resulting in competition between the labelled and the unlabelled immuno reactant and an immunosorption of labelled immuno reactant in an amount which is inversely proportional to the amount of unlabelled reactant in the sample.

Also in accordance with the invention, a process is provided for producing carrier-bound immunosorbents, in particular as described in the aforegoing which comprises applying a film of cross-linkable protein or peptide material to a solid carrier body to envelop the body, including a desired immuno reactant incorporated in or on the surface of the film and cross-linking the film and covalently bonding the immuno reactant to the film, preferably with one or more cross-linking or bifunctional linking reagents.

Some of the teachings relating to the process, in particular as to quantities and some of the substances to be used emerge from the earlier description herein of the immunosorbent according to the invention and need not be repeated.

In contrast to some prior art, embodiments of the present invention rely on physical envelopment or engagement by the film with the surface of the carrier body rather than on direct chemical reaction with the surface.

This physical engagement is preferably enhanced by a roughened surface texture. For example, the surfaces of glass beads are advantageously roughened by abrasive action, e.g. with silicon carbide powder until the beads are frosted.

The appended claims are to be considered a part of the present disclosure. In the following the invention and in particular the process will be explained more fully with reference to the accompanying drawing.

BRIEF DESCRIPTION OF THE DRAWINGS

The drawing illustrates diagrammatically a preferred embodiment of the process according to the invention for manufacturing immunosorbents according to the invention. In the diagram products according to the invention are illustrated schematically as well as a preferred use of such product.

DETAILED DESCRIPTION OF PREFERRED EMBODIMENTS

Referring to the drawing,

In the first process step denoted as I glass beads 1 (of which only one is shown) which could have a diameter of say 0.05 mm to 15 mm, but which in the present example are 6 mm in diameter are thoroughly cleaned by washing and degreasing if necessary. The beads could be ovaloid or ellipsoidal but are preferably spheroidal, more particularly spherical, They are then—step II—shaken with silicon carbide abrasive powder until the surface 2 has assumed a frosted, non-transparent finish. To clean the surfaces the beads are placed in concentrated hydrochloric acid and boiled for 5 minutes (alternative cleaning methods, e.g. with hot chromic acid are obviously possible). After cooling the beads are washed with distilled water. Residual acid is neutralised by boiling the beads for 10 minutes in a 10% sodium carbonate solution. After cooling the beads are washed repeatedly with deionised water, filtered through a 0.25 micron filter, dried in a warming oven and cooled again.

In step III a first immunoreactant is applied as a "first layer". The immunoreagent is assumed to be itself of a protein or peptide character and is thus suitable to serve also as the film-forming protein or peptide material. It is applied to the beads in the form of an aqueous solution in a concentration of e.g. 1 to 30, preferably 1 to 20 mg/ml. 0.1M saline or buffer is a suitable aqueous medium. The immunoreactant is either a selected protein- or peptide-type antigen (e.g. a viral antigen) or an antibody or a protein or peptide molecule which has an affinity for a "second layer" antibody or antigen, (e.g.

Protein A or concanavillin A). In this example a layer of antibodies 3 of a selected specificity is applied as a "first layer", e.g. sheep IgG anti-rabbit IgG (if the "second layer" is rabbit IgG) or sheep IgG anti-IgY (if the second layer is IgY—recovered from egg yolks). 75 glass beads 1 are placed in a plastic Petri dish with 1 ml of the "first layer" antibody solution (approximate concentration 20 mg/ml—see Example 1). The beads are gently rolled in the antibody solution to moisten them evenly and then successively rolled similarly in a further five dry plastic Petri dishes to dry off excess antibody solution. As stated earlier, if it is desired to lower the concentration of immunosorbtive sites on the bead surface or if the amount of antibody available is small, a lower antibody content of the solution may be employed, and in order to provide sufficient film-forming material the antibody content of the solution is extended with suitable protein or peptide, e.g. 30-1000%, preferably not more than 300% by weight based on the amount of antibody. Suitable film-forming extenders are for example gelatine, albumin, lactalbumin, partially hydrolysed proteins.

In step IV the "first layer" of antibodies is crosslinked in the present embodiment with glutaraldehyde vapour (saturated). A 25% glutaraldehyde solution is placed in a flat glass dish to a depth of 5 mm, covered tightly with aluminium foil and left standing for a few hours to allow the atmosphere above the solution to saturate. The glass beads of step III are then placed in a Petri dish and floated on the glutaraldehyde solution. The glass dish is tightly covered again, and the beads are exposed to the vapour (at ambient room temperature of about 18° to 25° C.) for 1 hour or longer. This time parameter is to some extent interrelated with: (a) concentration of "second layer" antibodies used (see step VI) to form the "second layer", and (b) length of incubation time for the absorption (immunosorption) of the "second layer" antibodies. Many different combinations of these parameters give good results and the following should be considered for guidance only, particularly since the desired amount of antibody in the "second layer" is also dependent on the intended use of the immunosorbent. For example, if the immunosorbent is to be adapted for a specific assay, e.g. a radio-immuno assay (RIA) or enzyme-linked immunosorbent assay (ELISA), the preferred amount of antibody required to bind a substance to be determined (e.g. a hormone or drug) falls within limits which are generally known or can be determined readily.

Useful exposure times are in general in the range of 20 minutes to 3 hours at room temperature (18°-25° C.). Usually between 30 minutes and 180 minutes, say 60 to 120 minutes gives good results, particularly when the remaining parameters (a) and (b) are of the order of magnitude as described further below. 60 minutes to two hours exposure in step IV results in a good "single layer" product for general use. Increasing the concentration of the "second layer" antibodies (parameters a)) in step VI and/or increasing the immunosorption time for the "second layer" (parameter b)) has the effect of lengthening the optimum recommended time of exposure and vice versa.

The combination of these parameters determines the number of available immunosorption sites per glass bead which in turn has an optimum value for any particular intended use of the bead. It is possible to determine the number of such available immunosorption sites e.g. by measuring the amount of radioactively labelled immunoreactant which is immunosorbed by the product.

After cross-linking it is (except as described further below) generally necessary—step V—to remove or block any excess of functional groups of the cross-linking agent (diagrammatically indicated by whisker-like lines 4a). In the case of aldehydes such as glutaraldehyde a reactive amine such as ethanolamine may be used. Before doing so, it is preferred to wash off (e.g. with water or dilute saline) any uncombined cross-linking agent. Thereafter the beads are placed in 1% aqueous ethanolamine, e.g. of moderated alkalinity by being dissolved in a dilute buffer such as 0.1M phosphate buffer at pH 7.6. One hour is generally found sufficient to block excess aldehyde groups. Approximately 100 ml solution is used for 75 beads. Unreacted ethanolamine is washed off by washing three times with phosphate buffer (50 ml, 0.1M, pH 7.6). Glycine has been used as an alternative to ethanol amine but is less preferred.

The beads 1a thus prepared represent one embodiment of an immunosorbent according to the invention and are suitable as an intermediate for further processing as described below. They comprise a film 4 ("first layer") of cross-linked protein or peptide including or wholly composed of cross-linked antibodies 3 enveloping the bead 1. These antibodies 3 are randomly orientated in the "first layer" film 4. However, some of the antibodies 3a are so orientated that their antigen capturing sites face and project outwardly from the film, sufficiently to serve as immunosorption sites. The "blocked" glutaraldehyde chains are denoted as 4b.

It is desirable that the number of immunosorbent sites available in the "first layer" of antibodies should be about half the number of antigens to be captured thereby because the strongest immunosorption occurs if each antibody captures two antigens.

The product of step V can be stored for long periods, preferably in the cold, e.g. at 4° C.

The product of step V (either after storage or immediately) is converted into a "double layer" embodiment of the invention in step VI by the application of a "second layer" of immunoreactant. The "second layer" immunoreactant in this example is a different type antibody which on the one hand is antigenic to the antibodies of the "first layer" and which on the other hand is specific to a particular hapten (e.g. being a substance which is to be determined in an immunosorbtive assay). For example the substance to be assayed is the thyroid hormone $T_3$, "first layer" antibody is sheep IgG raised against rabbit IgG and the "second layer" antibody is to be a rabbit IgG which is specific against $T_3$. Or the "first layer" antibody is sheep IgG raised against IgY (from egg yolk) and the "second layer" antibody is IgY recovered from the egg yolk of eggs from fowl hens actively immunised against $T_3$. The conditions of step VI are so selected (empirically) that the antibody concentration in the "second layer" is suitable for the intended purpose of the immunosorbent. The following principles apply:

1. For an assay such as RIA the amount of antibody must always be smaller than the amount of antigen tested for. Otherwise the assumption that the bound radio-actively labelled antigen is inversely proportional to the amount of unlabelled antigen will not hold.

2. The amount of "second layer" antibody captured by the "first layer" depends on the avidity (binding properties) and amount of antibodies in the "first layer", the concentration of the "second layer" antibody solution, the time of exposure thereto and the temperture.

3. The number of "second layer" antibody molecules available for capturing by the "first layer" should, however, be at least twice the number of exposed antibody sites in the "first layer" to achieve strong immunosorption of the "second layer" antibody molecules.

4. The number of antibody molecules forming the "second layer" in turn should be so limited that at least two antigens are available for capturing by each of the "second layer" antibody molecules under the conditions of eventual use of the "double layer" immunosorbent.

5. Nevertheless, the period of contact of the "first layer" with the "second layer" antibody solution should be so limited that some "first layer" antibodies remain unoccupied.

On the basis of the aforegoing principles the antibodies for the "second layer" are applied in amounts of 1 to 20 μg per bead preferably 2-5 μg, e.g. 2 μg in the case of sheep or rabbit IgG and fowl IgY against $T_3$. The antibodies are dissolved in phosphate buffer (0.1M, pH 7.6) in a volume sufficient to cover the beads completely. The exposure of the beads to the antibody solution takes place between 0° C. and the denaturing temperture of the antibodies (about 56° C.), provided at least part of the exposure is carried out at a low temperature at which a peculiar effect occurs (apparent a change in molecular configuration) which results in a strong retention of the "second layer" by the "first layer". The total exposure time required is temperature dependent, higher temperatures accelerating the formation of the "second layer". In the preferred procedure the solution is preheated (on a waterbath) to a predetermined luke warm temperature, more particularly between 30° and 40° C., in particular 37° C. The glass beads 1a are then added to the prewarmed solution, and the predetermined temperature is maintained for a predetermined first exposure period. This period is best determined empirically and is generally from 1 to 3 hours depending on temperature, concentration of antibody solution and avidity of the "first layer" antibodies. At the preferred temperature of 37° C. the optimum is usually between 1.5 and 2 hours, more particularly 1.7-1.8 hours. Either too short or too long a period of exposure was found to have an adverse effect on the sensitivity of assays such as RIA carried out with the beads.

Superior results are attained if the beads in the antibody solution are then cooled to a lower temperature, preferably between 0° and 10° C., e.g. 3°-5° C., say 4° C. followed by a second period of exposure to the solution at the lower temperature. This second period is similarly optimised empirically and is generally between 10 and 60 minutes (the higher the temperature the shorter the period,) preferably between 20 and 40 minutes, say 30 minutes at 4° C.

The resulting beads 1b are then removed from the solution and washed three times with phosphate-buffered saline solution. The latter preferably contains some surfactant. Between 0.05 and 1% polyoxyethylene sorbitol mono-oleate (commercial products Tween 20 or Tween 80), preferably 0.1% as the surfactant has a stabilising effect on the antibodies, particularly on IgY antibodies. The beads 1b are then ready for immediate use in an assay or may be stored for later use, preferably at low temperature, e.g. 4° C. They comprise a "first layer" 4 in the form of a cross-linked film including antibodies 3, some of which 3a face and project outwardly. A major portion of these "first layer" antibody molecules 3a have captured two each of the "second layer" antibody molecules 5 (drawn in faint lines to distinguish them from antibodies 3 which are drawn in heavier lines). Antibodies have an approximately Y-shaped configuration, the head of the Y representing the capturing site (each of which immunosorbs two antigens) the stem (or tail end) of the Y of the antibodies 5 contains the antigenic determinants for which the antibodies 3a of the "first layer" are specific. Accordingly, the antibodies 3a hold the captured pairs of antibodies 5 of the "second layer" by the tail end to result in a preferential orientation of antibodies 5 with their capturing sites radially outwardly directed. This is in contrast to the random orientation of the "first layer" antibodies 3,3a.

The diluted "second layer" antibody solution can be used repeatedly but must be stored at low temperature (4° C.).

The beads 1b may be supplied commercially as a kit together with other chemicals, reagents and standards required for a particular assay. In the case of a radioimmuno assay (RIA) the kit would include standard samples of the substance to be determined and an amount of the same substance (or a substance immunologically indistinguishable therefrom) which has been labelled radioactivity (e.g. with $^{14}C$ or tritium or $^{125}I$).

In the drawing step VII diagrammatically illustrates what happens in an RIA for $T_3$ thyroid hormone.

A solution (standard solution or unknown sample) buffered to pH 8.6 with 0.06M barbitone buffer, containing a known or unknown quantity of ordinary $T_3$ and a further known quantity of $T_3$, labelled with radioactive $^{125}I$, is preheated (on a water bath) to a specified moderately warm temperature (e.g. 37° C.). A "double-layer" coated bead 1b is added to the solution and kept therein at the specified temperature for a specified period, e.g. 2 hours. The solution, with the bead inside, is then cooled to a specified low temperature which is maintained for a further specified period (e.g. 4° C. for 30 minutes). The solution is removed from the bead. The bead is washed, e.g. three times with e.g. phosphate-buffered saline (preferably containing 0.1% Tween 20). The bead is then placed in a counting vial and the radioactivity is counted for one minute in a gamma-counter. The gamma count is directly proportional to the amount of radioactively labelled $T_3^*$ immunosorbed by the bead 1c in step VII. As shown in the drawing those "second layer" antibodies 5 which have captured (immunosorbed) antigen 6 have done so in respect to both "normal" $T_3$ as well as radioactively labelled $T_3^*$, namely in a ratio of $T_3^*:T_3$ which is proportional to that ratio in the sample, provided the total amount of antigen in the solution exceeds the maximum capturing cacpacity of the antibodies 5 on the bead 1b. In that case the measured radioactive count is inversely proportional to the amount of $T_3$ in the sample.

As described above, the immunoreactant itself may provide wholly or partly the material of which the film is formed or it is supplemented with an additional protein or peptide type of film-forming material or such additional film-forming material is used to form the film proper, the immunoreactant being covalently bonded to the film, e.g. by means of the bifunctional reagent or reagents. To carry out the last-mentioned modification, step III described with reference to the drawing is modified in that the solution of antibodies 3 is initially totally replaced by a solution of film-forming protein or peptide, e.g. gelatine. This is followed by cross-linking, e.g. as in step IV resulting in a film having only partly reacted chains of cross-linking agent attached thereto. Step V is then replaced by "blocking" the unreacted linking groups of the cross-linking agent by reaction with reactive sites of antibodies 3. This procedure may be advantageous if the amounts of antibody 3 available are small, when a higher proportion thereof may remain available to provide immunosorbtive sites on the film surface.

The cross-linking or bifunctional linking reagent or reagents must have at least two functional groups of which at least one is covalently reactive to enter into a bonding with a reactive site of the immuno reactant whilst at least one further functional group which may be the same or different, must be reactive to enter into a covalent bonding reaction with a reactive site of whatever protein or peptide material or materials serves or serve as the film-forming material.

If the functional groups of the linking reagent are different, the one group is preferably specifically selected to react with a specific type of reactive site on the immuno reactant whilst the other is specifically selected to react with a specific type of reactive site useful for bonding to the film forming material. Many immunoreactants are likely to have several types of reactive sites of which some are likely to be more involved than others in the peculiar and specific immuno activity of such immuno-reactant, i.e. more specifically involved in immunosorbent reactions. For that reason the choice of type of site most suitable for bonding the immuno-reactant whilst preserving a maximum of its specific desired immunological properties, should be made with due regard to this principle, if necessary by simple experiment with different linking reagents.

Typical functional groups of linking reagents are:

| Functional groups | Reacts with |
|---|---|
| Aldehyde | primary amines |
| Imide | primary amines |
| Amino | aldehyde |
| Cyano (as in cyanogen bromide) | hydroxy groups |
| Halogen (e.g. bromine) | thiol or hydroxy groups |
| Carboxyl groups | primary amines |
| Activated carboxyl groups (e.g. N—Succinimidyl esters of carboxylic acids) | primary amines hydroxy groups |
| Anhydrides (e.g. Succinicanhydride and maleic anhydride) | primary amines |
| Maleimide derivatives | thiol groups |

Suitable examples of such linking reagents are:
Dialdehydes, in particular aliphatic dialdehydes, preferably glutaraldehyde and its higher homologues having from 4 to 20 carbon atoms between successive carbonyl groups;
Carbodiamines, preferably compounds wherein the amine groups are separated by at least three, but preferably by from 4 to 20 carbon atoms, e.g. hexamethylenediamine;
cyanogen bromide, which reacts in the first step with any —OH groups of one partner to form activated imido-esters which in turn react in the second step with the amino groups of the second partner, e.g. antigens or antibodies.

The aforesaid linking reagents may be caused to react with the respective reactive sites in manner known per se, more particularly as set out in the aforegoing table.

In some embodiments of the process the linking reagent may first be reacted with one of the two partners to be grafted together to form a reactive intermediate which is then reacted with the other partner. The first said partner may either be the immuno reactant or the film-forming material.

Alternatively, both partners may each react (e.g. separately) with a linking compound to form reactive intermediates which intermediates in turn are then reactively bonded together.

If the immuno reactant lacks a reactive group suitable for the covalent bonding reaction with the difunctional linking compound, a reactive derivative is formed by introducing such reactive group by appropriate reaction, e.g. with a different bifunctional linking compound. The same applies if it is considered undesirable to sacrifice any of the existing reactive groups of the immuno reactant for the bonding reaction, because their preservation is considered important for a desired immunosorbic reaction. Thus in the above described modification of the example illustrated in the drawings (where a cross-linked protein film is first formed in steps III and IV, followed only in step V by the bonding of antibody to the unreacted linking groups attached to the film) it is sometimes advantageous to react the immunoreactant to be introduced into the "first layer" (either an antibody 3 or a hapten to an antibody which is to be immunosorbed by the "first layer") with a linking compound to produce an intermediate which reacts particularly readily with the unreacted linking groups of the film.

It may be advantageous for reasons of geometry and improved immunosorbtive properties to select a linking compound or compounds adapted to provide a relatively long linking chain, e.g. an aliphatic carbon chain of preferably at least three, and up to say 20, more preferably from four to ten carbon atoms between the immuno reactant and the film.

Although in the aforegoing the use of difunctional organic linking compounds has been particularly stressed, it will be appreciated by those skilled in the art that other means and methods of linking or cross-linking can be used, such as free radical methods, e.g. radiation induced, or direct condensation reactions (between the film-forming protein and the immuno-reactant) without the insertion of a linking molecule.

In the following examples thyroid hormone assays are particularly emphasised. One reason is the relatively advanced state of development thereof, whereby an understanding by those skilled in the art of the examples of embodiments of the invention for the same purpose is facilitated. In addition there still exists a need for the development of even better thyroid assays. The present invention affords new avenues to such improvement.

However, those skilled in the art will readily understand how the teachings of the examples can be applied analogously to an almost inlimited variety of assays useful in clinical diagnosis, forensics or pharmacokinetic studies (e.g. on high potency drugs where blood levels are too low for measurement by more conventional methods), provided antibodies specific against the substance to be assayed are available or can be produced. For this purpose use is made either of conventional techniques or of the teachings cross-referred to in the present application. The examples should be read in the context of the present specification as a whole.

EXAMPLE 1

Glass beads 6 mm in diameter are first roughened according to step II described above.

Step III is carried out with IgG prepared as follows:

Blood is drawn from the jugular vein of sheep or from the main artery supplying the ears of rabbits. This blood is allowed to clot at room temperature for 3 to 5 hours, followed by centrifugation at 3000×g for 30 minutes to remove the fibrin clot and all cellular materials. The clear blood serum thus obtained is diluted with 2 volumes of borate buffer (0.01M, pH 8.6). Polyethylene glycol (PEG 6000) is added to a final concentration of 15% m/v. The suspension is centrifuged at 12,000×g for 10 minutes. The precipitate pellet is removed and resuspended in the same volume of borate buffer (0.01M, pH 8.6). PEG is again added to a final concentration of 15% m/v and the suspension is centrifuged at 12,000×g for 10 minutes. The supernatant is discarded and the pellet is dissolved in half the original serum volume in phosphate buffer (0.1M, pH 7.6).

For carrying out step III as described above, the IgG solution which has a concentration of 20 mg/ml is used (1 ml for 75 glass beads). Cross-linking takes place with glutaraldehyde as described with reference to step IV of the drawings by 60 minutes exposure to saturated glutaraldehyde vapour at 20° C. followed by ethanolamine treatment as described with reference to step V of the drawings.

EXAMPLE 2

The same procedure as described in example 1 is adopted for coating glass beads with IgY from egg yolk. The IgY is isolated as follows:

The egg yolks are separated from the egg white and are thoroughly washed in a stream of water to remove as much of the egg white as possible. The yolk sacks are kept back while the yolk is dropped into a funnel supported on a measuring cylinder. The volume of the yolk is measured and the volume of 0.1M phosphate buffer (pH 7.5) equivalent to 2 volumes of yolk is added and thoroughly mixed. Pulverised PEG 6000 is added to a final concentration of 3.5% m/v. The mixture is stirred until the polymer has dissolved and is then centrifuged at 14,000 g for 10 minutes to cause the separation of three phases in the centrifuge tubes: a yellow fatty layer on the surface, a clear supernatant layer and a semi-solid pliable bottom layer of casein-like vitellin, representing about one third of the total volume of the substance in the centrifuge tubes. The supernatant fluid including the fatty layer is carefully decanted into a funnel containing a tight plug of absorbent cotton in the neck of the funnel to filter off the lipid. The volume of the clear filtrate is measured and more pulverised PEG 6000 is added to adjust the concentration to 12% m/v, thereby to completely displace the IgY from solution. The precipitate is centrifuged off at 14,000×g for 10 minutes. The pellets are redissolved in phosphate buffer equivalent to the original volume of yolk and the IgY is once again precipitated with 12% m/v PEG 6000 and centrifuged as before. The supernatant including the PEG is removed by suction. The final pellets are redissolved in the volume of buffer equivalent of 1/6 of the original volume of yolk. The protein concentration is now 20 mg/ml. 0.01% sodium azide is included in the buffer for preserving the isolated IgY.

EXAMPLE 3

The procedure according to example 1 is also followed if a "first layer" of proteinaceous antigens is to be applied to the glass beads instead of antibodies. Examples of such antigens are: bacteria, bacteria fragments carrying the bacterial immunogenic determinants, purified viruses, viral antigens, proteins, drugs, hormones and toxins. In the case of non-protein drugs or hormones, these are first attached to a carrier protein, preferably gelatin prior to the coating step. The coating step is carried out with a solution of 1 to 20 mg per ml of proteinaceous antigen.

EXAMPLE 4

Rabbit IgG is prepared by immunising rabbits against egg yolk IgG in a conventional manner. Glass beads are coated with the rabbit IgG in the manner described in example 1. The glass beads thus coated are then immersed in a buffered solution (pH 7.6) containing 1–20 mg/ml (typically 2 mg/ml) of egg yolk antibodies (IgY) specific against viral antigen "X". After 30 minutes immersion with gentle agitation, the glass beads are thoroughly washed with saline containing 0.1% Tween 20 (a commercially available surfactant) or PBS (phosphate buffered saline) containing 0.1% Tween 20 or other non-ionic surfactant agent to remove any non-adhering IgY. The "double layer" specific antibody preparation thus produced may be stored as follows:

The coated glass beads, while moist, are kept in a stoppered glass container at 4° C. Alternatively the beads are dried in a dessicator or equivalent apparatus over a dessicant at 4° C. $P_2O_5$ is a suitable dessicant.

In order to determine viral antigen "X" in an aqueous solution the following test is carried out:

One bead is placed in a micro titration tube to which is added 0.3 ml of the solution to be tested. The tube is gently agitated for 5 minutes at room temperature. In this manner the virus becomes immobilised by the specific antibody attached to the glass bead. The beads "loaded" with captured virus are washed with PBS containing 0.1% Tween 20 and then immersed in 0.3 ml of an aqueous solution containing 0.01–0.1 mg of specific antibody against antigen "X", (e.g. Bromegrass mosaic virus) labelled with an enzyme (more particularly the enzyme alkaline phosphatase). These antibodies attach themselves to the trapped virus particles in proportion to the number of virus particles trapped. The enzyme-labelled IgY is to be prepared as follows:

1 mg alkaline phosphatase is dissolved in 1 ml IgY solution (2 mg/ml protein). 0.2 ml 0.25% solution of glutaraldehyde in saline is added. Leave standing at room temperature for 2 hours and then dialyse against phosphate-buffered saline (PBS) for 16 hours. Then dilute with PBS to 0.5%.

The enzyme used for labelling the antibody is capable of producing a colour reaction with paranitrophenyl phosphate, the substrate of the enzyme, the intensity of which colour reaction can be measured colorimetrically to give a measure of the amount of enzyme present, which in turn in the present case is a measure of the amount of virus trapped. The colour reaction may be carried out either on the amount of enzyme removed from the reagent solution by attachment to the glass beads (after washing off any unattached excess) or on the amount of enzyme left behind in the solution after the removal of the glass beads.

In a preferred procedure a 12-well titration plate is used. 0.1 ml saline (with Tween) is pipetted into each well. 0.1 ml of the IgY enzyme complex is added to the saline in the first well. A dilution series is made by transferring 0.1 ml from the first well to the second, similarly from the second to the third etc. A coated bead is then added to each well and incubated at 37° C. for 1 hour. The beads are removed and thoroughly washed with PBS. p-nitrophenyl phosphate dissolved in buffer (97 ml diethanolamine, 800 ml water, 0.20 g NaN3, HCl to adjust pH to 9.8 made up to 1 L) is brought to a concentration of 1 mg/ml. 0.1 ml of this solution is placed in each of 12 clean wells of a micro titration plate and the beads are placed into the wells in correct sequence. The plate is incubated at room temperature for 2 hours.

This is a modification of the so-called "Elisa" test. It is applicable to all antigen-antibody reactions, e.g. the following: bacteria, viruses, proteins, toxins.

EXAMPLE 5

The same types of glass beads coated with rabbit IgG raised against egg IgY is used as in the previous example. Also the step of attaching a specific type of antibody against an antigen "X" proceeds as in the previous example. However, in the following modification of an Elisa assay, the sample containing antigen "X" to be determined is mixed with an equal volume of solution containing an appropriate concentration of antigen "X" labelled with enzyme (which can be the same enzyme as in Example 4). Normally 0.1 mg/ml of antigen "X" is the maximum. In effect, the amount of fluid which attaches to a glass bead is small. Therefore hundreds of beads may be covered with 1 ml of one of the immune reagents.

In this procedure there is competition between the labelled antigen and the unlabelled antigen in the test sample, and the amount of enzyme labelled antigen "X" which becomes attached to the specific antibodies on the surface of the glass bead is inversely proportional to the concentration of non-labelled antigen "X" derived from this sample. The colorimetric determination, either of the amount of enzyme attached to the glass bead or of the amount of enzyme left behind in the solution proceeds as in the previous example.

The procedure according to the present example is suitable for antigens, having a molecular weight of between 300 through $8 \times 10^6$ and even higher, including bacteria.

EXAMPLE 6

6 mm glass beads are coated with sheep IgG anti-rabbit IgG as "first layer" according to the procedure described in Example 1. For producing the "second layer" (step VI according to the drawings) a commercial anti-T3 rabbit whole serum produced by Henning AG, Berlin, Federal Republic of Germany is used. This freeze dried product is reconstituted with distilled water to the original volume and diluted with phosphate buffer in a ratio of 1:320.

The procedure is carried out as described above for step VI at 37° C. for 1.75 hours followed by 30 minutes at 4° C. The beads are removed from the antibody solution, washed as previously described three times with a PBS solution containing 0.1% Tween 20.

RIA tests for T3 are carried out as follows:

The assays are performed in polypropylene pill vials of 10 mm inner diameter with a rounded bottom in triplicate for each unlabeled T3 concentration.

Standards are made up in buffer to have the following T3 concentrations:

0.05 ng/ml, 0.7 ng/ml, 2 ng/ml and 5 ng/ml.

To each assay tube the following is added:
i. Assay buffer (100 μl, 0.1M phosphate buffer pH 7.6)
ii. $^{125}IT_3$ solution in assay buffer (100 μl)
iii. Standard T3 solution in assay buffer (100 μl)

The contents of each tube are mixed by gentle tapping. The tubes are preheated in a water bath to 37° C. The abovedescribed "double coated" glass beads are added to the solution, one bead to each tube. The tubes are incubated for 2 hours at 37° C. followed by a further 30 minutes at 4° C. The fluid content of each tube is sucked off, and the bead is washed three times with PBS solution (0.1% Tween-1 ml per bead). The beads are placed in counting vials and "counted" for 1 minute in a gamma counter.

The T3 RIA on unknown blood serum samples is performed as follows:

To each assay tube the following is added:
i. assay buffer (100 μl, barbiturate buffer 0.06M, pH 8.6)
ii. $^{125}IT_3$ solution in assay buffer (100 μl)
iii. assay buffer (100 μl) containing 0.1% poluol.
iv. thyroxine binding globulin (TBG) inhibitor in assay buffer (100 μl)
v. standardised serum or unknown serum (50 μl)

To produce T3 standardised sera, T3—free sera are produced and predetermined amounts of T3 are added.

The same concentrations of T3 standard as used in the assay of T3 in buffer are used in the assay in sera, i.e. 0.05 ng/ml, 0.7 ng/ml, 2 ng/ml, 5 ng/ml. A standard curve is prepared for these values.

In other respects the assay procedure is precisely the same as described further above for the T3 solutions in buffer.

EXAMPLE 7

Example 6 is repeated, modified as follows:

The glass beads are coated with sheep IgG-anti IgY as a first layer in the manner described in example 1.

For the second layer IgY-anti T3 is recovered from the egg yolk of immunised hens and recovered in accordance with the procedure described in example 2. The anti T3 antibodies are further concentrated, prior to the coating step by the following procedure: The anti-T3 IgY antibody preparation is dialysed against 0.2M acetic acid for 4 hours to lower the pH to approximately 4. The solution is cooled to 4° and the pH adjusted to 4.6. PEG 6000 is added to a concentration of 8% m/v and the precipitate which forms is centrifuged off at 14,000×g. The pH is then raised to 5.0 by the addition of 0.1M sodium hydroxide and the PEG concentration is again adjusted to 8% m/v. The precipitate which forms is centrifuged off and is recovered as a concentrate of IgY molecules with a high T3 binding capacity. This concentrate is dissolved in PBS, pH 7.6 to form a solution containing 1 mg/ml protein. The further procedure is as in example 6. The enrichment or fractionation of specific antibodies by precipitation with PEG or the like with pH control is applicable to mamalic antibodies as well. The correct pH for recovering a specific fraction and the optimum concentration of precipitant should be determined empirically.

EXAMPLE 8

Glass ballotini (bead diameter 0.05 to 0.1 mm) are roughened and coated as described in example 1 with 5% human IgG dissolved in PBS. The beads are packed into a small column, IgY anti-human IgG (recovered as described in Example 2) 100 mg in 5 ml was applied to the column (25 cm × 1.5 cm packed with 20 g ballotini coated with 0.1 g human immuno-globulin) and allowed to percolate in slowly. The unbound protein was removed by washing with PBS until the eluate showed a negative reaction with 7% perchloric acid. The IgG-IgY complex was dissociated and the IgY was eluted with PBS containing propionic acid to lower the pH to 3.8. The eluate was concentrated to 2 ml by perosmosis against saturated polyethyleneglycol. The eluate had the expected IgY activity.

0.1% Tween 20 should be added to the PBS throughout the experiment.

EXAMPLE 9

Example 8 was repeated, modified in that the glass ballotini were coated with 2 ml anti-albumin IgY (20 mg/ml) in the manner described in example 2. 2 ml IgG anti-IgY was applied and allowed to percolate in slowly. The column was washed with phosphate buffer pH 7.2 to remove unbound IgG. The specific IgG antibody with dissociated from the IgY antigen with propionic acid and propanol (pH 3.6). The eluate was collected in a beaker which contained 10 ml sodium bisphosphate (0.2M) to neutralise the propionic acid immediately. The salt was removed against dialysis against PBS for 24 hours. IgG anti-IgY was recovered from the column.

EXAMPLE 10

Hens are immunised against thyroxine ($T_4$). IgY anti-$T_4$ is recovered from the egg yolk of the immunised hens in accordance with the procedure described in example 2. These antibodies are coated onto the "first layer" of 6 mm glass beads as described in example 1.

A volume of 200 μl IgY anti-thyroxine ($T_4$) is pipeted into six glass tubes. An IgG anti-IgY covered glass bead prepared as described above is placed into each tube and incubated at 37° C. for one hour. The beads are then washed with PBS containing 1% Tween 20, 1% polyvinylpyrrolidone and 0.2% ovalbumin.

Radioactively labelled $T_4$ and non-radioactive $T_4$ are added as follows:

| Tube no. | 125 I-$T_4$ (μl) | *cold $T_4$ (ml) | cold $T_4$ (μg) |
| --- | --- | --- | --- |
| 1 | 0,2 | 0,05 | 5 000 |
| 2 | 0,2 | 0,02 | 2 000 |
| 3 | 0,2 | 0,01 | 1 000 |
| 4 | 0,2 | 0,005 | 500 |
| 5 | 0,2 | 0,002 | 200 |
| 6 | 0,2 | 0,0 | 0 |

*The concentration of the "cold" (non-radioactive)$T_4$ was 10 μg/0,1 ml.

The beads were then removed blotted dry on filter paper and placed in a scintillation vial and the radioactivity was determined. The radioactivities measured were inversely related to the concentrations of non-active $T_4$ in the sample.

EXAMPLE 11

A solution is prepared containing 20 mg/ml of gelatine and 1 mg/ml of protein A (a protein derived from Staphylococcus aureus which possesses the ability to bind immunoglobulins of a considerable variety of origins).

Step III of the procedure described with reference to the drawing is modified by using the above solution in place of the IgG solution. The cross-linking step (step IV) and the "blocking step" with ethanol amine (step V) are carried out exactly as described with reference to the drawing.

Beads coated in this manner are then used to immobilise antibodies to which protein A has an affinity. This is done as described in Example 6. The amount of "second layer" antibodies must be previously decided upon and this in turn will determine the optimum concentration of "second layer" antibody solution and the duration of exposure of the bead to such solution. This is done empirically from case to case.

The aforesaid procedure can also be carried out with Concanavillin A instead of protein A.

EXAMPLE 12

A "first layer" coat is applied as described with reference to step III of the drawings by one of the following procedures:

(a) application of an IgG solution or IgY solution as described in Example 1 and 2 respectively (b) application of a solution of IgG or IgY with between 30 and 300% by weight of gelatine or albumin extender (based on gammaglobulin)

(c) Application of pure carrier protein such as albumin or gelatin (employed in a solution of 20 mg of gelatine or albumin per ml).

The beads thus coated (but not yet cross-linked) are dried in vacuo. A solution is prepared of 2-20 mg/ml of the diester of glutaric acid (or pimelic acid) prepared by condensation of N-hydroxysuccinimide using dicyclohexyl carbodiimide (J. Am. Chem. Soc. 86, 1839–1842, (1964)). 75 beads are placed in 10 ml of the cross-linking solution. The extent of cross-linkage can be controlled by the exposure time which is generally between 1 and 18 hours. The beads are washed and unreacted reactive groups are blocked with mercapto ethylamine (1% in phosphate buffer 0.1M, pH 7.6) for one hour—except in the case of (c) above where the blocking step is replaced by immersion of the beads in the solution of the "first layer" immunoreactant to be applied to the film.

"Second layers" of the desired "second layer" immunoreactant are then applied as described in example 6 or 7.

In this example glutaric and pimelic acid diesters with N-hydroxysuccinimide react with amine groups on protein molecules with the liberation of N-hydroxysuccinimide.

EXAMPLE 13

Example 12 is modified by using as the bifunctional cross-linking reagent 1,3 bismaleimido propane having the following structural formula:

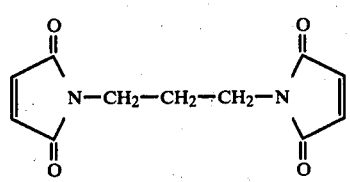

This reagent is prepared according to the method of Goodfriend et alia (Science, 144, 1344–1346 1964)). As for the remainder the procedure is the same.

The bismaleimides react with sulphydryl groups of proteins and similar molecules by adding onto the double bonds on the maleimide rings.

An unreacted maleimide derivatives are subsequently blocked by treatment with mercapto ethylamine.

EXAMPLE 14

Example 12 is modified by using as the bifunctional cross-linking reagent the N-hydroxysuccinimide ester of N-(4)-carboxycyclohexylmethyl)-maleimide.

The reactions occurring in that case are a combination of the reactions involved in example 12 and 13.

EXAMPLE 15

Example 12 is modified by using as the bifunctional cross-linking reagent, the N-hydroxysuccinimide ester of 3(2-pyridyl-dithio)-propionic acid of the formula

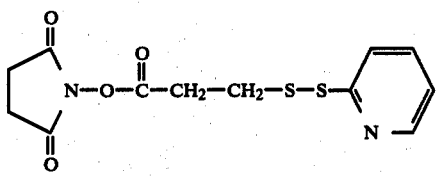

In this example amine groups of protein or the like react with the one end of the cross-linking agent with the elimination of N-hydroxysuccinimide whilst the other end reacts with sulphydryl groups by way of disulphide exchange, with the elimination of 2-mercapto-pyridine.

Blocking of unreacted functional groups is once again carried out with mercapto ethylamine.

EXAMPLE 16

Bovine gammaglobulin is reacted with N-succinimidile 3-(2-pyridyldithio) propionate (SPDP) according to the procedure of Carlson et alia (Biochem. J. 173, 723–737 (1978)). Excess SPDP reagent is removed by extensive dialysis. In the reaction amino groups of the gamma-globulin react with the SPDP with the elimination of N-hydroxysuccinimide to result in a reactive intermediate carrying the reactive 2-pyridyldithio group.

Glass beads are coated with cross-linked gelatin as described in Example 12. Reactive linking groups are introduced as follows:

182 mg dithiodiglycolic acid (dtdg) is dissolved in 1 ml of 2 molar sodium hydroxide. The dtdg solution is diluted to 25 ml with borate buffered saline (pH 6). 75 beads coated with gelatine as aforesaid, the gelatine having been cross-linked with glutaraldehyde and excess aldehyde groups having been blocked with ethanol amine, are then placed in the above solution and a further solution containing 250 mg of 1-ethyl-3(3-dimethylaminopropyl) carbodiimide (edci) in 2.5 ml of water is added with mixing. Mixing is continued over a period of 30 minutes at room temperature. The beads are then washed then four times in 50 ml of phosphide buffered saline (containing 0.1% Tween 20).

The glass beads so treated are then subjected to reduction by dithiothreitol (dtt). 0.5 ml of freshly prepared 1M dtt is diluted with 15 ml of phosphate buffered saline and 75 glass beads treated as aforesaid are added and allowed to react for one hour with occasional mixing. The beads are then washed four times with phosphate buffered saline (0.1% Tween 20) followed immediately by the next step.

A solution of 2 mg of the above described bovine gamma-globulin intermediate is prepared in 10 ml phosphate buffered saline and the freshly prepared treated glass beads are added. The reaction is allowed to proceed overnight at 25° C. The glass beads carry as reactive groups the moiety—NH—CO—CH$_2$—SH. The SH group reacts with the dithiopyridyl group, with the elimination of 2-mercapto pyridine. The resulting glass beads which now have the bovine gammaglobulin molecules covalently coupled to the gelatine coating are washed four times with phosphate buffered saline containing 0.1% Tween 20.

EXAMPLE 17

Example 6 is modified. Instead of anti-T$_3$ rabbit whole serum a rabbit antiserum against alpha-feto-protein (AFP) is employed for the "second layer".

The "double-layer" glass beads is used in combination with $^{125}$I-labelled AFP for conducting RIA determinations for AFP is amniotic fluid or in serum. The procedure is essentially as prescribed for commercial radioimmuno assay kits (e.g. "Gamma-Dab" (R) by Baxter Travenol Labs. Inc.). However, the present invention offers the great advantage that the inconvenient step, precipitation with liquid reagents, centrifugation and decantation in order to recover the pellet for gamma-counting is replaced by immunosorption on the glass bead which is then subjected to counting.

EXAMPLE 18

Example 17 is modified using sheep IgG-anti IgY as a first layer as in Example 7. IgY is recovered from hens immunised by the method of Polson against AFP conjugates prepared as described in South African patent application No. 81/4898 and corresponding applications in USA, UK, Japan and Federal Republic of Germany. The IgY has a higher avidity, $K=2\times 10^{11}$ L/mole than conventional antibodies of rabbit origin ($6.0\times 10^9$ L/mole).

EXAMPLE 19

Glass beads are coated with Gelatine cross-linked with glutaraldehyde and the excess aldehyde groups are blocked with ethanol amine as described for stages I to IV with reference to the drawings, gelatine (20 mg/ml) being used instead of the solution of gammaglobulin.

The iodohistamine ester of testosterone hemi-succinate is prepared according to the method of Tantchou and Slaunwhite, J. of Immunoassay, 1(1), 129–147 (1980), as described there on page 139 under the heading "Reaction of iodohistamine with activated esters". 5 mg of the ester are dissolved in 20 ml PBS and the 75 gelatine coated glass beads are then coated with that solution. The beads are thereafter spread out in a Petri dish and exposed for 5 minutes to ultraviolet light (wave length 211 nm—mercury lamp) whilst being caused to roll around gently in the dish. Thereafter the glass beads are washed with PBS containing 0.1% Tween 20.

Although in the aforegoing examples the invention has been exemplified with reference to glass beads it will be understood that beads or other suitable supporting bodies can be used of materials other than glass without the coating procedure having to be changed in any material respects.

What is claimed is:

1. A carrier-bound immunosorbent comprising a solid carrier body carrying an immobilized immuno-reactant, wherein the immunoreactant, being either an antigen or an antibody, is covalently bonded to a crosslinked proteinaceous film enveloping the carrier body in such a manner that immunologically active parts of the immunoreactant are present on its surface in a form in which they are available for immunosorption, wherein said film consists essentially of protein, partially hydrolysed protein, peptide or a combination thereof, crosslinked in situ with a crosslinking agent on the surface of the carrier body into a coherent film enveloping the surface and clinging thereto.

2. An immunosorbent according to claim 1, wherein immunologically active parts of the immuno reactant are exposed and project from the film.

3. An immunosorbent according to claim 1, wherein the film is predominantly cross-linked protein molecules.

4. An immunosorbent according to claim 3 wherein the immuno reactant itself provides the protein molecules or peptide portions or at least a substantial part thereof.

5. An immunosorbent according to claim 1, wherein the film includes a cross-linked additional protein or peptide film-forming substance other than the immuno reactant.

6. An immunosorbent according to claim 1 wherein the immuno-reactant has a molecular or particle mass of from 300 to $8 \times 10^6$ and higher in the case of bacteria and is bonded to the film in an amount of from 0.6 to 500 mg/m$^2$ of surface area of the carrier body.

7. An immunosorbent according to claim 6 wherein the film contains between 30 and 1000% by weight of protein or peptide extender based on the weight of immunoreactant.

8. An immunosorbent according to claim 1, wherein the carrier body takes the form of a rod or bead.

9. An immunosorbent according to claim 8 wherein the carrier body is a solid bead having a density higher than 1 g/cc.

10. An immunosorbent according to claim 1, wherein protein A or concanavillin A is covalently bonded to the film and in its turn carries selectively captured antibody molecules, held by the tail ends of the molecules.

11. An immunosorbent according to claim 1, wherein the film carries covalently bonded thereto a first immuno reactant being one member of an antigen/antibody pair, the first immuno reactant holding by antigen/antibody interaction the second member of the pair, this second member projecting from the surface with a region thereof which itself in turn has a desired immuno reactivity for entering into an immunosorbent reaction with a third immuno reactant.

12. In a carrier-bound immunosorbent comprising a carrier body carrying an immobilized immunoreactant, the improvement wherein at least the surface of the carrier body is non-porous; wherein a film coated thereon on the surface of the carrier carries covalently bonded thereto a first immunoreactant being one member of an antigen/antibody pair, the first immunoreactant holding by antigen/antibody interaction the second member of the pair, this second member projecting from the surface of said immunosorbent with a region thereof which itself in turn has a desired immunoreactivity for entering into an immunosorbent reaction with a third immunoreactant; and wherein the first immunoreactant forms a covalently bonded part of a film consisting essentially of protein, partially hydrolysed protein, peptide, or a combination thereof, crosslinked in situ with a crosslinking agent on the surface of the carrier body into a coherent film clinging to said surface.

13. An immunosorbent according to claim 12 comprising a first layer including covalently bonded and cross-linked antibodies of a first species of animal elicited against antibodies of a second species of animal and a second layer immunosorbed on the first layer of specific antibodies elicited against a specific antigen in the second species of animal.

14. A carrier-bound immunosorbent which is specific to a specific antigen comprising a carrier body carrying an immobilised immuno reactant, comprising on a solid substrate a first layer including covalently bonded and cross-linked antibodies of a first species of animal elicited against antibodies of a second species of animal and a second layer immunosorbed on the first layer, of specific antibodies elicited against the specific antigen in the second species of animal; and wherein said solid substrate is non-porous, or said first layer covers the substrate substantially completely.

15. An immunosorbent according to claim 14, wherein the antibodies of the first layer are randomly orientated and the antibodies of the second layer are predominantly radially outwardly orientated with their antigen capturing regions facing outwardly.

16. An immunosorbent according to claim 14, wherein the second species is a fowl.

17. An immunosorbent according to claim 16 wherein the antibodies elicited in the fowl have been recovered from the egg yolk of an egg or eggs of such bird.

18. A diagnostic or analytical reagent, comprising an immunosorbent according to claim 1.

19. A reagent according to claim 18, adapted to be used for radio immuno assays or enzyme-linked immuno assays.

20. A process for preparing a carrier-bound immunosorbent, which comprises applying a film of crosslinkable protein, partially hydrolysed protein, or peptide material to the surface of a solid carrier body to envelop the body, including a desired immunoreactant incorporated in or on the surface of the film, and crosslinking the film in situ while on the surface of the carrier body, the crosslinked film thereby formed clinging to the carrier surface, and covalently bonding the immunoreactant to the film.

21. A process according to claim 20, wherein the immunoreactant itself provides wholly or partly the material of which the film is formed.

22. A process according to claim 20, wherein the immuno reactant is supplemented with an additional protein or peptide type of film-forming material.

23. A process according to claim 20, wherein an additional film-forming material is used to form the film proper, the immuno reactant being covalently bonded to the film.

24. A process according to claim 20, wherein a cross-linking or bifunctional linking reagent is used for cross-linking the film and/or for bonding the immuno reactant to the film.

25. A process according to claim 24, wherein said cross-linking or bifunctional linking reagent has in its molecule two or more functional groups, each of which is independently an aldehyde, imide, amino, cyano, halogen, carboxyl, activated carboxyl, acid anhydride or maleimide group.

26. A process according to claim 24, wherein the linking reagent is first reacted with one of the two partners to be grafted together to form a reactive intermediate which is then reacted with the other partner.

27. A process according to claim 25, wherein the immuno reactant lacks a reactive group suitable for the covalent bonding reaction with the bifunctional linking compound; and wherein a reactive derivative is formed by introducing said suitable reactive group by reaction with a different bifunctional linking compound containing said suitable reactive group.

28. A process according to claim 20, wherein a free-radical intermediate is formed of the immunoreactant and the free radical intermediate reacts to become covalently bonded to the film.

29. A process according to claim 28, wherein the free-radical intermediate is produced by radiation.

30. A process according to claim 20, werein a first layer is formed having bonded to the film antibodies against antibodies for a second layer and wherein the carrier body including the first layer is exposed to a solution of the second layer antibodies until the required amount of the second layer antibodies has been immunosorbed by the first layer.

31. A process according to claim 30, wherein the number of said second layer antibody molecules available for capturing by the first layer is at least twice the number of exposed antibody sites in the first layer.

32. A process according to claim 30, wherein the exposure to the solution of said second layer antibodies takes place between 0° C. and the denaturing temperature of the antibodies, at least part of the exposure being carried out at a low temperature at which a change occurs which results in a strong retention of the "second layer" by the first layer.

33. A process according to claim 32, wherein the exposure takes place first at a relatively higher temperature where the immunosorption is accelerated, followed by further exposure at the low temperature.

34. A method of selectively removing an immunoreactive substance from a mixture in which it is present, which comprises contacting said mixture with an immunosorbent as claimed in claim 1 which carries exposed on its surface an immobilised immunoreactant specific to immunogenic determinants present on said immunoreactive substance and not present on other substances in the mixture, thereby selectively immunosorbing said immunoreactive substance, and removing the immunosorbent from contact with the mixture.

35. In a radio immuno assay (RIA) comprising the step of selectively removing an immunoreactive substance from a mixture in which it is present, the improvement wherein said substance is removed using a method according to claim 34.

36. In an enzyme-linked immuno assay (ELISA), comprising the step of selectively removing an immunoreactive substance from a mixture in which it is present, the improvement wherein said substance is removed using a method according to claim 34.

37. A method according to claim 34 which comprises, after removing the immunosorbent from contact with the mixture, desorbing the first substance to release it from the immunosorbent in purified form.

38. A method according to claim 34, wherein in said immunosorbent, said film carries covalently bonded thereto a first immuno reactant being one member of an antigen/antibody pair, the first immuno reactant holding by antigen/antibody interaction the second member of the pair, this second member projecting from the surface with a region thereof which itself in turn has a desired immuno reactivity for entering into an immunosorbent reaction with a third immuno reactant.

39. A method according to claim 34 which comprises intimately contacting the immunosorbent, having exposed on its surface a standard amount of a first immunoreactant specific to a complementary second immuno-reactant of an antigen/antibody pair with a solution of the second immuno-reactant, and determining the amount of the second immuno-reagent in the solution which becomes attached to the immunosorbent.

40. In a carrier-bound immunosorbent comprising a carrier body carrying an immobilised immuno reactant, the improvement wherein the surface of the carrier body or a film coated thereon carries covalently bonded thereto a double layer comprising a first layer of a first immuno reactant being one member of an antigen/antibody pair, the first layer holding by antigen/antibody interaction a second layer comprising the second member of the pair, this second layer in turn carrying on its surface in a form available for immunosorption molecular regions having a desired immuno reactivity for entering into an immunosorbent reaction with a third immuno reactant, at least one of the members of the pair being IgY.

41. An immunosorbent according to claim 40, wherein the second layer of the double layer comprises IgY.

42. A carrier-bound immunosorbent which is specific to a specific antigen, comprising a solid carrier surface carrying an immobilised immuno reactant, the immuno reactant being present in a double layer composed of a first layer comprising IgG specific against IgY and a second layer immunosorbed by the IgG comprising IgY which in turn is specific to the specific antigen.

43. An immunosorbent according to claim 42, wherein the first layer of the double layer is covalently bonded to the solid carrier surface.

44. An immunosorbent according to claim 43, wherein the solid carrier surface is non-porous.

45. A carrier-bound immunosorbent of high specificity, comprising a carrier body having a solid surface carrying a permanently adhering layer of protein, partially hydrolysed protein, peptide or a combination thereof, the layer comprising a covalently bonded and thereby immobilized immunoreactant, being either an antigen or an antibody, in such a manner that immunologically active parts of the immunoreactant are present exposed in a form in which they are available for immunosorption, and being essentially free of accessible pores and other nonspecific adsorption sites.

46. An immunosorbent according to claim 45 wherein the carrier body is solid.

47. An immunosorbent according to claim 45, wherein the layer is crosslinked.

48. An immunosorbent according to claim 47, wherein the layer is in the form of a coating crosslinked after application to the surface, consisting essentially of protein, partially hydrolysed protein, peptide or a combination thereof, and crosslinking moieties of a crosslinking agent rendering the film coherent and clinging to the surface.

49. An immunosorbent according to claim 45 wherein immunologically active parts of the immunoreactant project from the layer or coating.

50. An immunosorbent according to claim 3, wherein said protein molecules are partially hydrolysed.

* * * * *